United States Patent
Germain et al.

(10) Patent No.: US 7,521,231 B2
(45) Date of Patent: Apr. 21, 2009

(54) METHOD FOR PREPARING ENGINEERED TISSUE

(75) Inventors: Lucie Germain, St.-Augustin-De-Demaures (CA); François Auger, Sillery (CA); François Bergeron, Sainte-Foy (CA); Charles Roberge, Sillery (CA)

(73) Assignee: Organogenesis, Inc., Canton, MA (US)

( * ) Notice: Subject to any disclaimer, the term of this patent is extended or adjusted under 35 U.S.C. 154(b) by 297 days.

(21) Appl. No.: 10/522,010

(22) PCT Filed: Jul. 16, 2003

(86) PCT No.: PCT/CA03/01079

§ 371 (c)(1),
(2), (4) Date: Nov. 9, 2005

(87) PCT Pub. No.: WO2004/007699

PCT Pub. Date: Jan. 22, 2004

(65) Prior Publication Data

US 2006/0128010 A1   Jun. 15, 2006

Related U.S. Application Data

(60) Provisional application No. 60/396,004, filed on Jul. 16, 2002.

(51) Int. Cl.
*C12N 5/06* (2006.01)
*C12N 5/08* (2006.01)

(52) U.S. Cl. .................. 435/325; 424/422; 424/443; 435/366; 435/371; 435/395; 623/1.11; 623/23.72; 623/23.76

(58) Field of Classification Search ................ None
See application file for complete search history.

(56) References Cited

U.S. PATENT DOCUMENTS

| | | | | |
|---|---|---|---|---|
| 5,711,969 A | * | 1/1998 | Patel et al. ................ 424/551 |
| 5,885,619 A | * | 3/1999 | Patel et al. ................ 424/551 |
| 5,922,028 A | * | 7/1999 | Plouhar et al. ........... 623/23.72 |
| 5,955,110 A | * | 9/1999 | Patel et al. ................ 424/551 |
| 6,176,880 B1 | * | 1/2001 | Plouhar et al. ........... 623/13.17 |
| 6,479,618 B1 | * | 11/2002 | Vonderhagen ............ 528/274 |
| 6,503,273 B1 | * | 1/2003 | McAllister et al. ......... 623/1.41 |
| 6,773,713 B2 | * | 8/2004 | Bonassar et al. ........... 424/423 |
| 7,112,218 B2 | * | 9/2006 | McAllister et al. ......... 623/1.41 |
| 2003/0027332 A1 | * | 2/2003 | Lafrance et al. ............ 435/366 |
| 2004/0078090 A1 | * | 4/2004 | Binette et al. ........... 623/23.76 |
| 2005/0079604 A1 | * | 4/2005 | Germain et al. ............ 435/325 |
| 2005/0170501 A1 | * | 8/2005 | Auger et al. ................ 435/366 |
| 2007/0077232 A1 | * | 4/2007 | Naughton et al. ......... 424/93.2 |
| 2007/0111307 A1 | * | 5/2007 | Auger et al. ................ 435/325 |
| 2008/0108134 A1 | * | 5/2008 | Murphy et al. ............. 435/371 |

FOREIGN PATENT DOCUMENTS

| | | |
|---|---|---|
| WO | WO 96/31226 | 10/1996 |
| WO | WO 97/37613 | 10/1997 |
| WO | WO 99/05262 | 2/1999 |
| WO | WO 0029553 | * 5/2000 |
| WO | WO 00/69355 | 11/2000 |
| WO | WO 03/007795 | 1/2003 |
| WO | WO 03/045458 | 6/2003 |

OTHER PUBLICATIONS

Qing Ye, et al., "Tissue engineering in Cardiovascular surgery: new approach to develop completely human autologous Tissue," European Journal of Cardio-Thoracic Surgery, vol. 17, Apr. 2000, pp. 449-454, XP002959353.

L'Heureux Nicholas et al., "A Completely Biological Tissue-Engineered Human Blood Vessel," Journal Fed. of American Soc. For Experimental Biology, vol. 12, 1998, pp. 47-57. XP002942845.

Byung-Soo Kim et al., "Cyclic Mechanical Strain Mechanical Strain Regulates the Development of Engineered Smooth Muscle Tissue," Nature Biotechnolgy, Nature Publishing, US, vol. 27, No. 10, Oct. 1999, pp. 979-983, XP001145976.

Keiichi Kanda et al., "Mechanical Stress Induced Cellular Orientation and Phenotypic Modulation of 3-D Cultured Smooth Muscle Cells," Asaio journal, J.B. Lippincott Co., vol. 39, No. 3, Jul. 1, 1993, pp. M686-690.

Lopez, C.A. et al., "Peripheral Anchorage of Dermal Equivalents," British Journal of Dermatology, vol. 127, No. 4, 1992, pp. 365-371, XP009021181.

* cited by examiner

*Primary Examiner*—Herbert J. Lilling
(74) *Attorney, Agent, or Firm*—Edward J. Adamson; Ravi Dipali

(57) ABSTRACT

A method for preparing a human or animal tissue by applying a compressive force to a stack of sheets of living tissue thereby inducing adjacent layers to fuse or adhere to each other. The force is applied in direction normal to the surface of the tissue. A multi-layer tissue produced by the method described above can also possess at least two different types of sheets and/or consist essentially of between two and twelve sheets of living tissue. The method can also be used to prepare a planar tissue that can further be incorporated in a multi-layer tissue construct. The methods and tissues described herein are useful for the preparation of engineered tissues.

18 Claims, 3 Drawing Sheets

METHOD FOR PREPARING ENGINEERED TISSUE

CROSS REFERENCE TO RELATED APPLICATIONS

This application is the 371 National Phase of International Application No. PCT/CA2003/001079, filed Jul. 16, 2003, which was published in English under PCT Article 21(2) as International Publication No. WO 2004/007699. This application further claims the benefit under 35 U.S.C. § 119 (e) of U.S. provisional application No. 60/396,004 filed Jul. 16, 2002. All of these applications are incorporated herein by reference in their entirety.

FIELD OF THE INVENTION

The present invention relates to engineered tissue. In particular, the present invention relates to methods for making engineered tissue from sheets of living tissue.

BACKGROUND OF THE INVENTION

Tissue engineering may be used to recreate tissues and organs for grafting onto patients. Engineered tissues and organs can also serve as in vitro models. A variety of tissue engineering techniques are known, including tissue in-growth, seeding of cells on artificial or biodegradable scaffolds, and collagen gels. Among them, a new method of tissue engineering, known as the "self-assembly" method, has emerged (L'Heureux et al.; Michel et al.; Pouliot et al.). In the self-assembly method, cells are induced to secrete and organise an extracellular matrix and thereby form a sheet of living tissue. The self-assembly method takes advantage of the fact that fibroblasts can produce a suitable extracellular matrix when grown in the presence of ascorbic acid. To create multi-layer tissue constructs, sheets of living tissue can be stacked upon each other, folded upon themselves, or rolled on a tubular support.

The development of tissue engineering methods to produce reconstructed tissues has focused on the optimization of morphological and histological properties of the reconstructed tissues. Most tissue engineering research has focused on optimizing techniques for growing sheets of tissue. However, in many cases, it would be desirable to make reconstructed tissue comprised of several layers of tissue and/or layers of more than one type of tissue. Multi-layer tissue constructs are thicker and therefore stronger and since multi-layer tissue constructs can comprise more than one sheet of living tissue, they can be designed to more closely resemble the tissues that they are intended to replace. However, in order to create useful multi-layer tissue constructs, it is essential to be able to fuse adjacent layers of cell tissue together so that the layers are bonded together as firmly and reliably as possible and resist separation. If these layers of tissue are not fused together well, they may separate or come apart over time, for example, during handling or in the body of a patient.

Thus, it would be desirable to have a method for preparing multi-layered engineered tissue constructs with improved fusion between adjacent layers of tissue.

DESCRIPTION OF BACKGROUND ART

Ye et al. teach that mechanical stress can enhance the synthesis and secretion of the principal extracellular matrix protein, collagen, by fibroblasts, thereby increasing the mechanical strength of the stiffness of reconstructed tissue.

Ye et al. describe a method for applying mechanical stress wherein sheets of fibroblast cells are mounted on frames to apply tension. However, the reconstructed tissues produced by this method have significantly less collagen than does native tissue and therefore would not be expected to have mechanical properties that resemble native tissue.

Kanda et al. teach that mechanical stress induces cell orientation and phenotypic modulation of cultured smooth muscle cells.

L'Heureux et al. describe a method of making a tissue-engineered blood vessel (TEBV) by wrapping sheets of living tissue around a tubular support.

Lopez-Valle et al. describe the use of a continuous (as opposed to punctuated or discontinuous) anchor made of porous glass microfiber material, the pores of which trap collagen fibers and thereby induce organization of extracellular matrix and orientation of cells.

SUMMARY OF THE INVENTION

The current invention provides a method for improving the fusion between adjacent layers of living tissue in a multi-layered engineered tissue construct. The current invention further provides a method for making a sheet of living tissue suitable for use in preparing a multi-layered engineered tissue construct. Multi-layered reconstructed tissues produced by this method have improved fusion between layers of tissue and the layers of tissue are less likely to separate during subsequent manipulation.

Thus, in one aspect, the invention provides a method for preparing a human or animal tissue from at least one sheet of living tissue, the method comprising the steps of: (a) arranging the at least one sheet of living tissue to form a multi-layer stack of living tissue; and (b) applying a compressive force in a direction normal to the surface of the multi-layer stack of living tissue with a force-applying means at a pressure and for an amount of time sufficient to compress layers of tissue together for inducing adjacent layers of tissue to fuse or adhere to each other.

A particular preferred embodiment provides a method for producing a tissue by forming a multi-layer stack of living tissue arranged on a substantially flat support. More preferably, the multi-layer stack is formed by superimposing two or more sheets of living tissue and/or by folding a sheet of living tissue upon itself.

In a further embodiment, the method comprises another step where the multi-layer stack is then anchored to a substantially flat support surface with moveable anchors comprising weights or ingots, wherein the anchors are of a suitable weight for (1) applying sufficient tension across the sheet of living tissue to prevent shrinkage and/or maintain cellular differentiation and/or induce orientation of cells in at least one sheet of living tissue and (2) allowing contraction of at least one sheet of living tissue once a predetermined threshold of tension is exceeded across the sheet of living tissue. A force is then applied normal to the surface of the layers of tissue by way of a weighted device suitable for applying evenly distributed pressure to the surface of the multi-layer stack of tissue, the weighted device being at least partially permeable to culture medium, for inducing adjacent layers of tissue to fuse to each other.

In a preferred embodiment, the force-applying means in step (b) of the method comprises a weight device suitable for applying substantially evenly-distributed pressure to said multi-layer stack of living tissue, the weight device being at least partially permeable to tissue-culture medium.

In a further embodiment, the multi-layer stack of step (a) of the method is formed by rolling a sheet of living tissue on a tubular support and, more preferably, the force-applying means of step (b) comprises a tissue-culture medium permeable elastic sleeve.

There are many different types of sheets of living tissues that can be used with the method described herein. In an embodiment, the method utilizes a biopsy as a sheet of living tissue. In another embodiment, the method utilizes cells cultured in vitro as a sheet of living tissue. More preferably, the cells are embryonic stem cells, post-natal stem cells, adult stem cells, mesenchymal cells, hepatocytes, Islet cells, parenchymal cells, osteoblasts and other cells forming bone or cartilage, and nerve cells. The mesenchymal cells can either be fibroblasts, interstitial cells, endothelial cells, smooth muscle cells, skeletal muscle cells, myocytes, chrondocytes, adipocytes, fibromyoblasts, or ectodermal cells. In a further embodiment, the sheet of living tissue can also be a skin tissue, a corneal tissue, a cardiac valve tissue, a connective tissue and/or a mesenchymal tissue.

In another aspect, the invention also provides a multi-layer tissue made according to the method described herein, wherein the multi-layer tissue comprises at least two different types of sheets of living tissue. In a preferred embodiment, the tissue consists essentially of between two and twelve sheets, more preferably of between three and nine sheets. In another embodiment, the tissue has a thickness of between about 0.01 mm to about 0.5 mm, more preferably of between about 0.03 mm to about 0.45 mm.

In a further aspect, the invention provides a method for preparing a planar human or animal tissue suitable for use in making a multi-layer tissue construct from at least one sheet of living tissue, the method comprising the steps of: (a) arranging said at least one sheet of living tissue on a substantially flat support surface; and (b) anchoring said at least one sheet of living tissue to the support surface with an adjustable anchor-means comprised of a multiplicity of spaced apart anchors, wherein the anchors are suitable for (1) applying sufficient tension across the sheet of living tissue to prevent shrinkage and/or maintain cellular differentiation and/or induce orientation of cells in said at least one sheet of living tissue and (2) allowing contraction of said at least one sheet of living tissue once a predetermined threshold of tension is exceeded across the sheet of living tissue.

Preferably, the adjustable anchor-means is comprised of discrete moveable anchors such as weights or ingots. Alternatively, the adjustable anchor means may also comprise a moveable frame or a multiplicity of moveable anchors mounted on a frame.

In a particular preferred embodiment, a planar construct can be made by forming a multi-layer stack of living tissue by superimposing two or more sheets of living tissue or by folding a sheet of living tissue upon itself. The multi-layer stack is then anchored to a substantially flat support surface with moveable anchors comprising weights or ingots, wherein the anchors are of a suitable weight for (1) applying sufficient tension across the sheet of living tissue to prevent shrinkage and/or maintain cellular differentiation and/or induce orientation of cells in at least one sheet of living tissue and (2) allowing contraction of at least one sheet of living tissue once a predetermined threshold of tension is exceeded across the sheet of living tissue. A force is then applied normal to the surface of the layers of tissue by way of a weighted device suitable for applying evenly distributed pressure to the surface of the multi-layer stack of tissue, the weighted device being at least partially permeable to culture medium, for inducing adjacent layers of tissue to fuse to each other.

In a further embodiment, the sheet of living tissue used to prepare the planar construct is obtained by culturing cells in vitro.

In yet another aspect, the invention provides a planar multi-layer tissue consisting essentially of between two to twelve sheets of living tissue obtained by the method described herein.

In another particular embodiment, a tubular construct can be made by forming a multi-layer stack of living tissue by rolling a sheet of living tissue onto itself, for example with the aid of a tubular support. A culture medium permeable elastic sleeve can be used to compress the layers of tissue in the multi-layer stack of living tissue together for inducing the adjacent layers of tissue to fuse to each other.

Other embodiments and advantages of the invention will become apparent from the detailed description to follow, together with the accompanying drawings.

All publications, figures, patents and patent applications cited herein are hereby expressly incorporated by reference in their entirety for all purposes to the same extent as if each was so individually denoted.

DETAILED DESCRIPTION OF THE PREFERRED EMBODIMENTS

In accordance with the present invention, it has been found that application of a compressive force normal to the plane of a sheet of tissue enhances fusion between adjacent layers of sheets of tissue. Compression improves contact between layers of tissue and encourages fusion of the layers of tissue. By way of example, a weighted device (for example, a sponge upon which spaced apart weights are placed) may be applied to a stack of two or more superimposed planar sheets of tissue, thereby applying a force normal to the plane of the sheets of tissue (see FIG. 1B). In another example, a suitably sized elastic sleeve can be fitted over a multi-layer stack of tissue made by rolling at least one sheet of tissue onto a tubular support, whereby the elastic sleeve applies pressure normal to the two-dimensional plane of the sheet of tissue (see FIG. 2).

Preferably, the compressive force or pressure is applied evenly on the entire tissue surface. Therefore, it is preferable that a device adapted to the shape of the tissue be used to induce the fusion. The amount of pressure applied to the surface of the tissue stack can be adjusted according to the needs of the engineered tissue. This pressure is applied for a period of time sufficient to allow the complete fusion of the tissue layers, preferably between 24 hours to 7 days.

It is also preferable that the device used to induce pressure to the surface of the tissue be permeable to culture media in order to allow the nutrition of the living cells. An acceptable way to generate this pressure on a flat tissue is to lay a semi-rigid sponge on the top of the tissue stack. Additional weight (for example, one or more solid ingots) can be distributed on top of the sponge to obtain the desired amount of pressure on the tissue (see FIG. 1B). Of course, any other system using mechanical or hydraulic pressure could be used to provide this compression.

In the example of a tubular or cylindrical construct, the compressing device should preferably apply equal pressure on the external surface of the construct. In this particular case, a good way to compress the tissue is to apply an elastic and permeable sleeve around the construct (see FIG. 2). The size and the elasticity of the sleeve can be adjusted to give the appropriate pressure for a given tissue.

Figure 2:
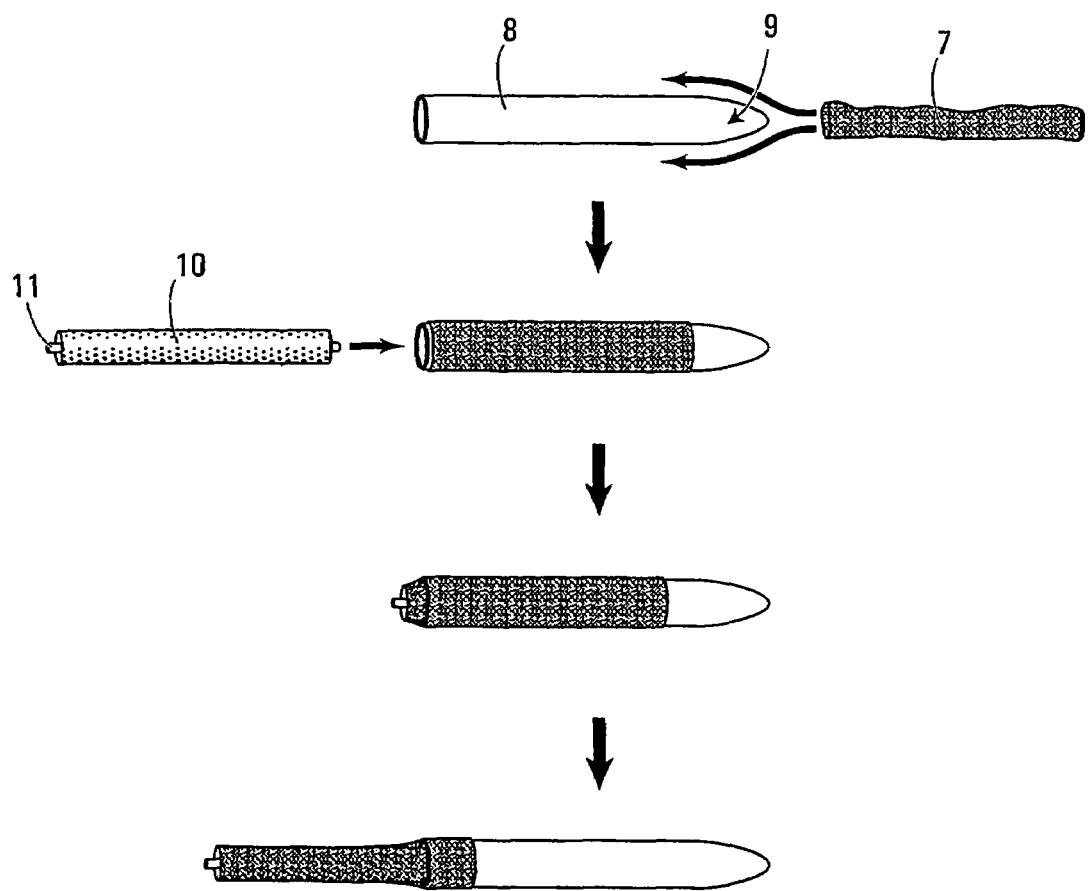
FIG. 2 illustrates a preferred method of compressing a tubular tissue construct. An elastic sleeve (7) is placed around a hollow tube (8) using its tapered end (9). The hollow tube (8) is larger than a tissue construct (10) which has been rolled around a mandrel (11). The hollow tube (8) is then placed around the tissue construct (10). The elastic sleeve (7) is transferred from the hollow tube (8) to the tissue construct (10) by gently displacing the tube (8) in one direction and the tissue construct (10) in the opposite direction.

To wrap the sleeve around the tissue and remove it without damage, an installation device may be used (see FIG. 2). The elastic sleeve (7) is mounted on a rigid hollow tube (8) using the tapered end of the tube (9). The tube, having an internal diameter slightly larger than the construct, is then passed over the tubular tissue (10) rolled around a mandrel (11). The end of the sleeve is then anchored to the mandrel and the hollow tube is carefully removed by pulling from the opposite side, gently depositing the sleeve on the tissue. To remove the sleeve without damaging the tissue, it may be for example carefully cut or unsewn.

It is known that mechanical stress may be used to induce cellular orientation and phenotypic modulation of cultured smooth muscle cells (Kanda et al.; Germain et al.). Thus, appropriate forces may be applied to maturating tissue in order to induce fiber orientation. Such forces may also prevent shrinkage and maintain the desired cell differentiation.

As an example, it has been shown that a continuous anchor, such as a frame or a ring of glass microfiber that circumscribes or encircles a tissue, may be used to induce cellular orientation (Ye et al.; Kanda et al.). The induction of cell orientation is thought to occur because the continuous anchor mechanically restricts the spontaneous contraction of the maturing cultured tissue, thereby creating a mechanical stress or tension across the tissue that induces cell orientation.

The underlying mechanism of the orientation response has not been well elucidated (Kanda et al.). However, when a continuous anchor is used, the tension across the tissue continues to build as the tissue matures and can reach levels that are detrimental to the health of the cells in the tissue, reducing viability of cells contained in the tissue and thereby producing an inferior tissue construct. Therefore, a continuous anchor, such as a rigid frame, may not be suitable for use with some tissue types, i.e. those tissues that can create a lot of tension as they mature.

Figure 1A:
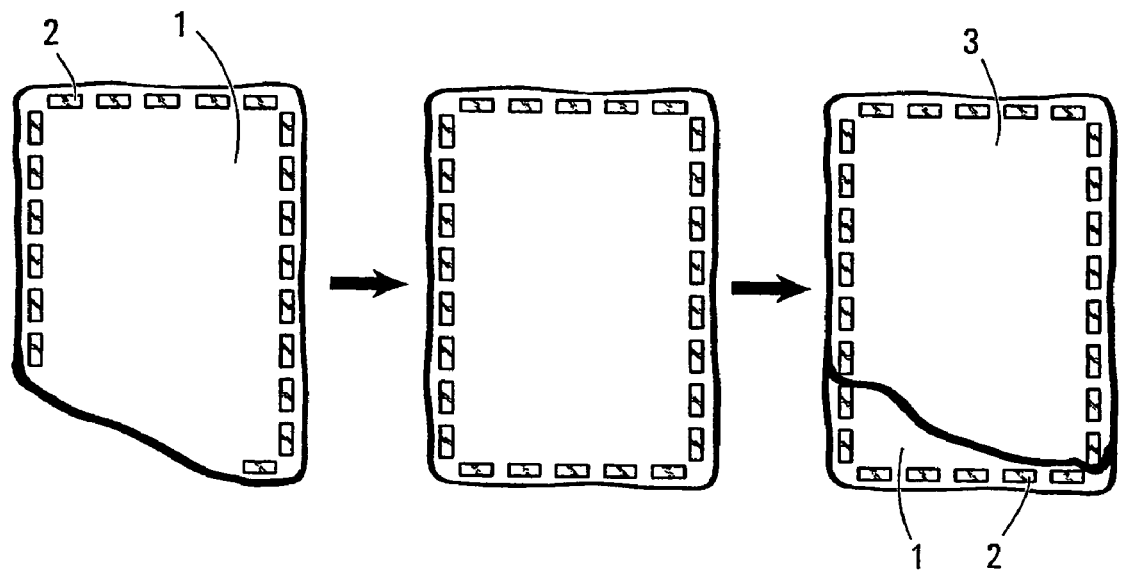
FIG. 1 illustrates a preferred method of making a planar tissue. (A) A first sheet of living tissue (1) is arranged on a substantially flat support surface and anchored peripherally with weights or ingots (2); a second sheet of tissue (3) is superimposed on the first sheet of tissue, and the weights or ingots (2) are moved, one-by-one, and placed on the second sheet, thereby anchoring the superimposed sheets. (B) A sponge (4) that has been cut to fit within the ingots is placed on top of the multi-layer tissue construct (5) so formed; and spaced-apart weights (6) are placed on the sponge.

The current invention provides an improved method of anchoring maturing cultured tissues, the method comprising an adjustable anchor means, preferably comprising a multiplicity of spaced apart anchors (such as moveable weights or ingots), wherein the anchors are suitable for (1) applying sufficient tension across the sheet of living tissue to prevent shrinkage and/or maintain cellular differentiation and/or induce orientation of cells in at least one sheet of living tissue and (2) allowing contraction of at least one sheet of living tissue once a predetermined threshold of tension is exceeded across the sheet of living tissue (for an illustration see FIG. 1A).

The anchor means is "adjustable" in that once the tissue has built up a tension higher than the maximum tension that can be held by the anchors (i.e. weights or ingots), the tissue can spontaneously contract and the anchors will be pulled along with the contracting tissue. Thus, the tension across the tissue cannot continue to build up when an adjustable anchor means as described is employed. The maximum tension that can build up across the tissue can be controlled by choosing suitable anchors (for example weights or ingots of a certain weight and number, or an adjustable frame that is designed to move in response to a certain tension or force). Thus, it is possible to optimize the amount of tension for any given tissue, for example, to enhance viability of cells in the tissue.

Anchors according to the current invention may be "discontinuous" or "punctual". A "discontinuous" or "punctual anchor" is a device that anchors a tissue substantially at a point in space. In contrast, in the context of the present invention, the term "continuous anchor" refers to a device for securing a tissue around its entire perimeter (such as described by Lopez-Valle et al.).

The anchors of the present invention may be "moveable" in that they can easily be placed on a sheet of tissue or removed therefrom.

For making planar sheets of living tissue for use in making multi-layer tissue constructs, it is preferred that anchors are arranged to form a closed perimeter near the edge of a sheet of tissue. This geometry induces cells and extracellular matrix fibers in the sheet of tissue to orient in the two dimensions of the plane of the sheet of tissue. This orientation of cells and extracellular matrix may be beneficial for fusion of adjacent layers of sheets of tissue and may also improve certain functional properties of the tissue. For example, in FIG. 1A, a first sheet of living tissue (1) is disposed on a flat surface and ingots (2) keep the first sheet in place. A second sheet of living tissue (3) is placed on top of the first sheet. Ingots are displaced from the first sheet and are arranged on top of the second sheet to anchor the stack of sheets. The ingots are arranged to follow the perimeter of the stack of living sheets. The ingots also provide a discontinuous mechanical force to the living sheets allowing cellular differentiation and contraction. The process may be repeated to obtain a multi-layer tissue construct.

The current invention provides the use of a multiplicity of spaced apart weights or ingots as anchors for applying mechanical force to tissue in a punctuated or discontinuous manner along the edge of the sheet of living tissue. If the weights or ingots are arranged very close to each other or so as to contact each other, they may displace each other somewhat when the tissue contracts. The amount and direction of mechanical force applied to a sheet of tissue can be controlled by varying the number, weight and position of the weights or ingots. Hence, it is possible to optimize or fine-tune the mechanical force conditions for any particular size or type of tissue.

The current invention is in contrast to the continuous anchor made of porous glass microfiber material described by Lopez-Valle et al. A porous continuous anchor like that described in Lopez-Valle et al. is not easily moved, removed or adjusted, and as a result, does not provide one with the ability to fine-tune the application of mechanical force to a tissue.

Weights or ingots for use as anchors according to the current invention may be made from any material that does not interfere with the development or differentiation of cells in the sheet of living tissue, such as stainless steel. Magnets or metal ingots coated with Teflon™ or any polymer material known in the art to be compatible with tissue culture may also be used. Suitable weight values for the weights or ingots for use with a tissue type can be determined empirically. Preferably, weights are chosen so that cell orientation and/or differentiation are induced.

The foregoing technique of using adjustable/moveable anchors and compression to fuse tissues together also may be used for producing three-dimensional tissue constructs.

Preparation of Sheets of Living Tissue

Sheets of living tissue for use in making multi-layered reconstructed tissue in accordance with the current invention may be obtained from biopsy or may be made using any known techniques. In the case where sheets of living tissue of mesenchymal origin are prepared using tissue engineering techniques, a preferred method is the self-assembly approach, which allows normal cell-cell and cell-extracellular matrix interactions. In addition, the self-assembly approach allows the secretion of important natural growth factors and cytokines, and the formation of a mature connective tissue necessary for functionality of the tissue and for the cells in the tissue to remain metabolically active and undergo normal mitosis.

The subsections below describe preparation and use of human engineered tissue in vitro. However, the invention is not limited to human engineered tissue and extends to animal tissue and engineered tissue with transformed (human and non-human) cells as well.

Cell Source

A variety of cells can be used in the human engineered tissue of the present invention. Preferred cell types include embryonic stem cells, amniotic fluid cells, post-natal stem cells, adult stem cells, mesenchymal cells, especially fibroblasts, interstitial cells, endothelial cells, smooth or skeletal muscle cells, myocytes (muscle stem cells), chrondocytes, adipocytes, fibromyoblasts, and ectodermal cells, including ductile and skill cells, hepatocytes, Islet cells, cells present in the intestine and other parenchymal cells, osteoblasts and other cells forming bone or cartilage, bone marrow cells and blood cells. In some cases it may also be desirable to include nerve cells.

Cells can also be genetically engineered to provide additional or normal function. Methods for genetically engineering cells with retroviral vectors, polyethylene glycol, and other methods known to those skilled in the art can be used.

Cells may be autologous, allogeneic or xenogeneic, however autologous or allogeneic cells are preferred. Immunologically inert cells, such as embryonic or fetal cells, stem cells, and cells genetically engineered to avoid the need for immunosuppression may also be used. Methods and drugs for immunosuppression are known to those skilled in the art of transplantation.

In some embodiments, cells are obtained by biopsy and dissociated using standard techniques, such as digestion with a collagenase, trypsin or other protease solution. For example, the dermal layer of a skin biopsy can be digested with collagenase according to the method of Germain and Auger. After the digestion of the dermal fragments, mesenchymal cells are harvested following centrifugation and expanded in cell culture media. All cell cultures are used between their fourth and eight passages, and kept incubated at 37° C. and 8% $CO_2$. Cells can be easily obtained through a biopsy anywhere in the body, for example, skeletal muscle biopsies can be obtained easily from the arm, forearm, or lower extremities, and smooth muscle can be obtained from the area adjacent the subcutaneous tissue throughout the body. The biopsy can be readily obtained with the use of a biopsy needle, a rapid action needle which makes the procedure extremely simple and almost painless. Cells may also be procured from, for example, blood vessels, blood, such as umbilical cord blood, valves and discarded tissues, such as foreskins and tissue obtained during esthetic or cosmetic surgical procedures.

Fibroblasts, such as dermal fibroblasts or adventitial fibroblasts, may be used. Fibroblasts are easily available, and they are the primary collagen secreting cells in connective tissues. Dermal fibroblasts are typically harvested from normal adult skin specimens removed during reductive breast surgery, or from neonatal foreskin. The potential of human fibroblasts for cardiovascular application is enormous for both allogeneic and autologous grafts since cells contained in one square-inch of foreskin can be used to grow many acres of tissue.

Preparation of a Sheet of Living Tissue

The engineered tissue of the present invention is formed from at least one sheet of living tissue. Each sheet of living tissue is comprised of cells and an endogenous extracellular matrix. The extracellular matrix is secreted by cells, such as mesenchymal cells, embryonic stem cells or adult stem cells, to name a few. When mesenchymal cells, such as dermal fibroblasts, are cultured in a planar culture substratum using L-ascorbic acid or a phosphate derivative of L-ascorbic acid (e.g. Asc 2-P), serum, and growth factors, they show an abundant synthesis of extracellular matrix proteins. This creates the basis of the endogenous extracellular matrix. L-ascorbic acid plays an important role since it is a cofactor for the hydroxylation of proline and lysine residues in collagen (Hata and Senoo), and also it increases both the rate of transcription of procollagen genes and stability of procollagen mRNA (Tajima and Pinnell). The extracellular material is comprised of different proteins, such as collagen type I, other collagen types (fibrillar and non-fibrillar), elastin, fibrillin, glycosaminoglycans (such as decorin), growth factors, and glycoproteins, to name a few.

In the context of the present invention, the resulting living tissue formed from the cells and the extracellular matrix as described above is called a "sheet of living tissue".

An exemplary embodiment of methodology for generating such sheets of living tissue is described in U.S. Pat. No. 5,618,718 by Auger et al. In summary, Auger et al. describe that dermal fibroblasts, at a concentration equivalent to $10^4$ cells/$cm^2$, are plated into 75 $cm^2$ sterile Petri dishes. Cell medium is supplemented with a 3:1 DMEM and Ham's F12 modified medium, fetal bovine serum, penicillin and gentamicin, and with an ascorbic acid solution. For example, a final ascorbic acid solution between 50-100 µg/ml can be used every other day. Culture conditions are kept at 92% air and 8% $CO_2$ at full humidity. Culture time is approximately three weeks. At the end of the maturation time, the sheet of living tissue spontaneously detaches from the substratum.

It can be appreciated that a variety of methods can be used to prepare the sheets of living tissue (e.g. Auger et al.; Ye et al.; L'Heureux et al.; Michel et al.; Pouliot et al.) and the present invention is not limited in scope by using one particular shape (i.e. thickness and size), cell type, origin, age, maturation time, component concentration, and culture conditions to generate the sheet of living tissue.

Preparation of Engineered Tissue

The engineered tissue of the present invention is formed from superimposing a plurality of individual sheets of living tissue. In an embodiment, the number of sheets varies between two and twelve. As described above, the sheets of living tissue are comprised of an extracellular matrix secreted by cells, such as mesenchymal cells. The extracellular matrix is produced with many in vivo-like properties including supramolecular organization of collagen. Collagen is not only processed, but is also cross-linked efficiently and the collagen fibrils are assembled into bundles. When the sheet is layered upon itself, for example by folding or wrapping, or a plurality of sheets are stacked or superimposed, a three-dimensional construct having desired structural characteristics is formed in culture.

In some embodiments, the sheets of living tissue are stacked in a cell culture dish, either directly superimposed or in an overlapping fashion. By overlapping, tissues of various shapes may be formed. For example, rectangular sheets of living tissue may be arranged in an overlapping fashion to create a circular layered tissue construct. Or, irregularly shaped cell cultured sheets may be stacked in a manner to form a regularly shaped tissue. In addition, the individual sheets may be stacked in the same orientation or the orientation of the sheets may be varied to create specific effects in the resulting tissue.

Alternatively or in addition, one or more sheets of living tissue can be folded to form a multitude of layers. For example, one sheet may be folded upon itself in an accordion-type fashion or in repeated halves to superimpose portions of the sheet upon itself. Or, two or more sheets may be stacked to form a multi-layer stack of tissue, which multi-layer stack of tissue may then be folded upon itself to create even more variety of layering.

Alternatively or in addition, a wrapping technique, such as wrapping a sheet around itself in the style of a cinnamon roll, can be used to create a multi-layer stack of tissue. It is possible to combine different/many techniques, for example by first creating a multi-layer stack of tissue by (1) layering more than one sheet of tissue and/or (2) folding a sheet or a multi-layer stack of sheets of tissue on itself, then wrapping the multi-layer stack of (1) or (2) around itself.

Figure 3:
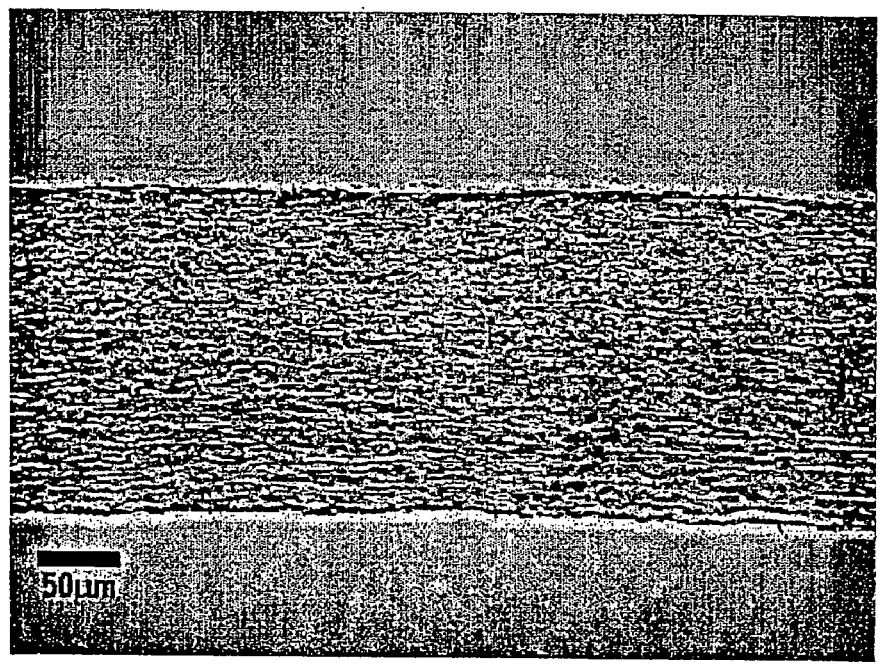
FIG. 3 is a microscopic view of the tissue made according to the method of the invention, after maturation. The tissue is assembled from nine sheets of living tissue containing fibroblasts and extracellular matrix constituents. Magnification 20×, scale bar 50 µm.

When layering, the sheets of living tissue are held together by surface adhesion between the sheets. Any number of sheets of living tissue may be used, preferably five or more, more preferably seven or more, and more preferably, nine, ten or eleven or more. The sheets are delicately handled with forceps and superimposed or otherwise assembled to form the human engineered tissue construct. By maintaining this construct in culture medium supplemented with ascorbic acid under conditions similar to those described in Huynh et al., the sheets of living tissue will fuse together to form a human engineered tissue resembling the corresponding mature tissue (FIG. 3).

For some applications, it is preferred that the resulting reconstructed tissue comprises more than one type of sheet of living tissue. For example, a reconstructed tissue suitable for use as a skin graft may comprise sheets of a dermal equivalent and epidermal equivalent. A reconstructed tissue suitable for use as a corneal graft should comprises the following layers: an epithelial equivalent; a stromal equivalent; and endothelial equivalent.

Maturation time of the construct will depend on the nature of the tissue and the specific mechanical properties desired. For example, it has been found that mechanical strength of certain tissue constructs plateau after seven weeks of maturation (L'Heureux et al.). For any given tissue construct, the maturation time necessary to obtain optimal functionality may be readily determined using routine methods known in the art.

Generally, the engineered tissue is thin enough to allow oxygen delivery through its surfaces to maintain metabolic needs yet thick enough to provide desired functionality. The current embodiments of the engineered tissue of the present invention are avascular, wherein the tissue does not include a microvasculature to deliver oxygenated blood to the tissue. Therefore, the tissue relies on oxygen diffusion from its surfaces to sustain the tissue. Due to oxygen diffusion limitations, the tissue thickness is currently an important consideration. (Weind et al.). The thickness of the engineered tissue may be controlled by choosing the number of sheets of living tissue used. The engineered tissue may have a thickness ranging from approximately 0.01 mm to 0.5 mm; more preferably between 0.03 mm to 0.45 mm. Preferred thickness will vary depending on the tissue type, intended function of the engineered tissue and the type of cells used.

If required, mature tissue constructs may be cut into a desired shape using any suitable method, such as die cutting and template cutting.

In an embodiment, cells from many different species and/or transformed cells can be used. Since it is contemplated that many applications of engineered tissue will concern treatment of human patients, human engineered tissue is especially preferred.

Preconditioning

If desired, the tissue-engineered construct may be preconditioned to reduce shrinkage, for example as described in the US application by Lafrance et al.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLE 1

Preparation of a Reconstructed Multi-Layered Human Tissue Construct from Sheets of Living Tissue Containing Fibroblasts and Extracellular Matrix Constituents.

The following example describes a method for preparing a reconstructed multi-layered human tissue construct from sheets of living tissue containing fibroblasts and extracellular matrix constituents according to the present invention (see FIG. 1 for illustration of the method). All of the procedures described below are done under sterile conditions, preferably using a sterile flow hood. It can be appreciated that a variety of methods can be used to prepare the multi-layered tissue construct and this example is not intended to limit the scope of this invention to the number of sheets of tissue superimposed, to one particular shape (i.e., thickness and size), cell type, origin, age, maturation time, component concentration, and culture conditions to generate the multi-layered human tissue construct. One skilled in the art can readily appreciate that various modifications can be made to the method without departing from the scope and spirit of the invention.

In this example, to produce a sheet of living tissue, 750,000 viable sub-cultured human skin fibroblasts are seeded in a standard 75 cm$^2$ sterile petri dish for a final seeding density of 10$^4$ cells/cm$^2$. Cells are fed with culture medium (DME containing 10% fetal calf serum (FCS), 100 IU/ml penicillin and 25 μg/ml gentamicin), and cultivated for 4 weeks to form sheets that can be manipulated. The culture medium is changed three times per week. A freshly prepared solution of ascorbic acid is added each time the medium is changed to obtain a final concentration of 50 μg/ml of ascorbic acid. During culture, cells are kept in a humidified atmosphere (92% air and 8% $CO_2$).

After the sheets of tissue are formed, they are peeled from the dishes, and three separate sheets of living tissue are superimposed using the following technique. A first sheet of living tissue is put into a petri dish and culture media is added over the sheet to keep it wet and to help to spread it. Stainless steel ingots (approximately 1 mm×2 mm×8 mm) are placed around the tissue sheet perimeter to keep the tissue sheet anchored and stretched to its maximal area on the surface of the petri dish. Another sheet of tissue is then placed on top of the first sheet of tissue. One by one, the ingots are carefully pushed aside from the first sheet and other ingots were placed around the tissue sheet perimeter of the second layer, spreading it over the first sheet of tissue. These steps were repeated to obtain a three-layered tissue construct.

Figure 1B:
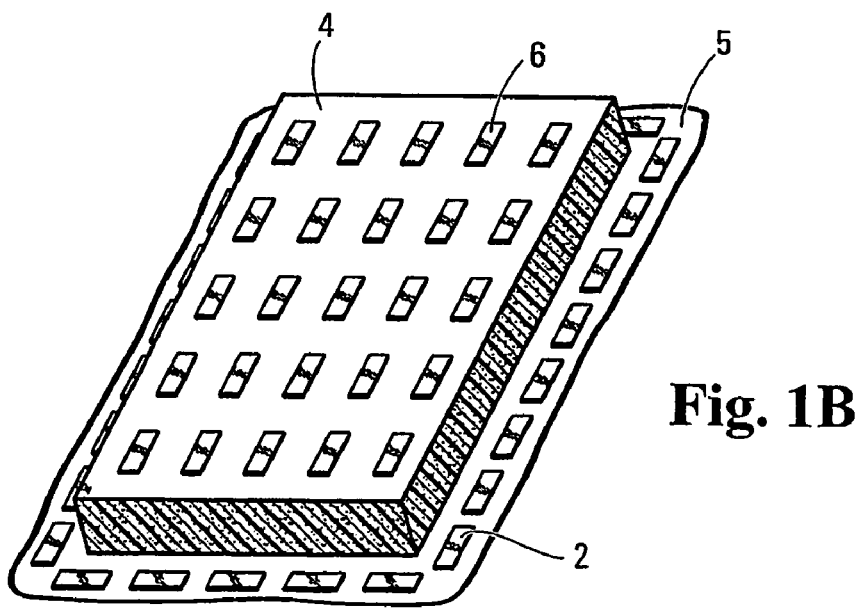

A semi-rigid sponge permeable to the culture media is then cut to fit the size of the tissue construct between the ingots and applied to the surface of the construct (see FIG. 1B). The sponge should closely fit the perimeter delimited by the ingots, but not overlap or exceed it. Ingots are then evenly distributed on the sponge surface to put some weight on it (in this case, 11 g/40 cm$^2$ [0.275 g/cm$^2$]). The sponge as well as the ingots are removed 24 hours to 7 days following the stacking.

Seven days after the stacking of the sheets of tissue, three three-layered tissue constructs were superimposed to form the final nine-layered tissue construct using the same technique as described above. The constructs were further incubated for up to 8 weeks and culture medium refreshed 3 times a week. The tissue constructs are then ready for shipment processing.

EXAMPLE 2

Microscopic Analysis of the Tissue Construct

The tissue construct is prepared according to the procedure described in Example 1. In this example, the tissue construct is assembled from nine sheets of living tissue.

Biopsies of the living tissue construct are first fixed in Bouin's™ solution. Cross-sections of the fixed tissue are embedded in paraffin. The cross-sections are stained with Masson's trichrome. Microscopic observations are done on a Nikon TS100™ microscope at 20× magnification.

FIG. 3 shows a microscopic cross-section of the tissue construct obtained after the stacking and maturation of 9 sheets of living tissue containing fibroblasts and extracellular matrix constituents. This light microscopy demonstrates a tissue construct resembling that of a native tissue with dense extracellular matrix. In addition, the 9 superimposed sheets of living tissue have fused together to form one single tissue construct.

EXAMPLE 3

Biomechanical Properties of the Tissue Construct

Mechanical properties of the tissue are determined by simple tensile tests and cyclic tensile tests. These tests are performed using a Tytron™ 250 MicroForce Testing System, (MTS Systems Corporation). This machine allows the loading and unloading of the tissue at different speed rates, and makes data acquisition of the stress and the deformation applied to the tissue. Both tests are made on 7.9 mm width tissue slices, for a total of three slices per tissue. Traction speed is set to 1 mm/s for both tensile and cyclic tests.

A simple tensile test consists in stretching the tissue until the load becomes high enough to break it. It allows the measure of the modulus of elasticity and the ultimate tensile strength of the tissue. These two values give the relative stiffness and resistance of the tissue.

Cyclic tensile tests allow determination of the percentage of plastic deformation of the tissue following a stretch. The percentage of plastic deformation evaluates the capacity of a tissue to recover its original shape after a load is applied to it. The cyclic tensile test is performed by stretching the tissue until 10% of the ultimate tensile strength of the tissue is reached. Then the traction is stopped and the load removed from the tissue at the same rate it was applied previously. This result gives the amount of irreversible deformation the tissue had to endure while it was stretched.

Figure 4:
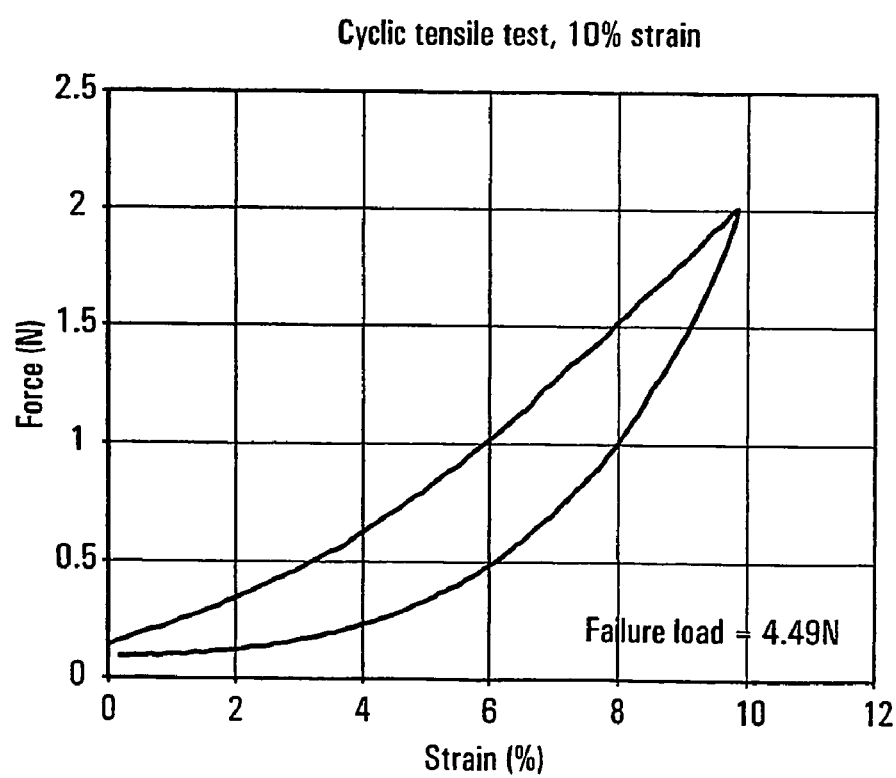
FIG. 4 graphs results of cyclic stress-strain test on a three-layer tissue construct made as described in Example 1.

FIG. 4 graphs cyclic stress-strain test on a mature three-layer tissue constructs made as described in Example 1. The tissue construct is resistant to tensile stress. It also has the capacity to recover its original shape after a 10% strain.

Throughout this application, various references are referred to describe more fully the state of the art to which this invention pertains. The disclosures of these references are hereby incorporated by reference in their entirety into the present disclosure for all purposes.

REFERENCES

Auger et al. U.S. Pat. No. 5,618,718 issued Apr. 8, 1997.
Germain and Auger. "Tissue engineered biomaterials: biological and mechanical characteristics", In: Wise, Trantolo, et al. editors: "Encyclopedic handbook of biomaterials and bioengineering", NY, N.Y.: Marcel Dekker Inc., 1995, pp. 699-734.
Germain et al. Patent application WO 03/045458, published Jun. 5, 2003.
Huynh et al. U.S. Pat. No. 5,928,281 issued Jul. 27, 1999.
Hata and Senoo. J Cell Physiol. (1989) 138,8-16.
Kanda et al. ASAI0 Journal (1993) 39, M686-90.
Lafrance et al. US application Serial No. 20030027332 published Feb. 6, 2003.
L'Heureux et al. The FASEB Journal (1998) 12, 47-56.
Lopez-Valle et al. British Journal of Dermatology (1992) 127, 365-371.
Michel et al. In Vitro Cell Dev Biol Anim (1999) 35, 318-26.
Pouliot et al. Transplantation (2002) 73, 1751-7.
Tajima and Pinnell. Biochem Biophys Res Commun. (1982) 106, 632-7.
Weind et al. J Thorac Cardiovasc Surg (2002) 123, 333-40.
Ye et al. European Journal of Cardio-thoracic Surgery (2000) 17, 449-454.

The invention claimed is:

1. A method for preparing a human or animal tissue from at least one sheet of living tissue, the method comprising the steps of: (a) arranging said at least one sheet of living tissue to form a multi-layer stack of living tissue; and (b) applying a compressive force in a direction normal to the surface of the multi-layer stack of living tissue with a force-applying means at a pressure and for an amount of time sufficient to compress layers of tissue together for inducing adjacent layers of tissue to fuse or adhere to each other, wherein said force-applying means in step (b) comprises an adjustable weighted device suitable for applying substantially evenly-distributed pressure to said multi-layer stack of living tissue, said weighted device being at least partially permeable to tissue-culture medium.

2. The method of claim 1, wherein said multi-layer stack is arranged on a substantially flat support.

3. The method of claim 1, wherein said multi-layer stack of living tissue in step (a) is formed by superimposing two or more sheets of living tissue.

4. The method of claim 1, wherein said multi-layer stack of living tissue is formed by folding a sheet of living tissue upon itself.

5. The method of claim 1, further comprising a step of anchoring said multi-layer stack of living tissue with anchoring means before said step (b) of applying a force, wherein said anchoring means applies sufficient tension across said multi-layer stack of living tissue to prevent shrinkage and/or maintain cellular differentiation and/or induce fiber orientation.

6. The method of claim 5, wherein said anchoring means comprises a multiplicity of spaced apart weights or ingots arranged substantially around the perimeter of said multi-layer stack of living tissue.

7. The method of claim 1, wherein the multi-layered stack of living tissue in step (a) is formed by rolling a sheet of living tissue on a tubular support.

8. The method of claim 7, wherein said force-applying means in step (b) comprises a tissue-culture medium permeable elastic sleeve.

9. The method of claim 1, wherein cells are obtained from said at least one sheet of living tissue, said at least one sheet of living tissue is obtained via biopsy.

10. The method of claim 1, wherein said at least one sheet of living tissue is obtained by culturing cells in vitro.

11. The method of claim 10, wherein said cells are selected from the group consisting of embryonic stem cells, post-natal stem cells, adult stem cells, mesenchymal cells, hepatocytes, islet cells, parenchymal cells, osteoblasts and other cells forming bone or cartilage, and nerve cells.

12. The method of claim 11, wherein said mesenchymal cells are selected from the group consisting of fibroblasts, interstitial cells, endothelial cells, smooth muscle cells, skeletal muscle cells, myocytes, chrondocytes, adipocytes, fibromyoblasts, and ectodermal cells.

13. The method of claim 1, wherein said at least one sheet of living tissue is selected from the group consisting of a skin tissue, a corneal tissue, a cardiac valve tissue, a connective tissue and a mesenchymal tissue.

14. A multi-layer tissue made according to the method of claim 1, wherein said multi-layer tissue comprises at least two different types of sheets of living tissue.

15. A multi-layer tissue according to claim 14, consisting essentially of between two sheets and twelve sheets of living tissue.

16. A multi-layer tissue according to claim 14, consisting essentially of between three sheets and nine sheets of living tissue.

17. A multi-layer tissue according to claim 14, wherein said tissue has a thickness of about 0.01 mm to about 0.5 mm.

18. A multi-layer tissue according to claim 17, wherein said tissue has a thickness of about 0.03 mm to about 0.45 mm.

* * * * *